(12) United States Patent
Lebrec et al.

(10) Patent No.: US 7,160,853 B2
(45) Date of Patent: Jan. 9, 2007

(54) PROTOCOL FOR PARACENTESIS

(76) Inventors: Didier Lebrec, 16 rue d'Alsace, Levallois-Perret (FR) 92300; Richard Moreau, 20 rue Mora, Enghieu les Bains (FR) 95880

( * ) Notice: Subject to any disclaimer, the term of this patent is extended or adjusted under 35 U.S.C. 154(b) by 518 days.

(21) Appl. No.: 10/380,153

(22) PCT Filed: Sep. 17, 2001

(86) PCT No.: PCT/EP01/11313

§ 371 (c)(1),
(2), (4) Date: Jul. 11, 2003

(87) PCT Pub. No.: WO02/24213

PCT Pub. Date: Mar. 28, 2002

(65) Prior Publication Data

US 2004/0102362 A1    May 27, 2004

(30) Foreign Application Priority Data

Sep. 15, 2000    (EP) .................................. 00402558

(51) Int. Cl.
*A61K 38/00*    (2006.01)
*A01N 37/18*    (2006.01)
(52) U.S. Cl. .......................................... 514/2; 530/315
(58) Field of Classification Search .................... None
See application file for complete search history.

(56) References Cited

OTHER PUBLICATIONS

Eyraud, et al., Anesth Analg. May 1999; 88(5): 980-984.*
Arroyo et al., J. Hepatol. 2000, vol. 32(suppl. 1): pp. 157-170.*
Zertova, M. et al., The Analogs of 8-D-Homoarginine-Vasopressin With *p*-Substituted Phenylalanine in Position 2; Synthesis and Some Biological Properties, Collect. Czech. Chem. Commune.(vol. 55) 1990.
Jans, D., et al., Biotinyl Analogues of Vasopressin as Biologically Active Probes for Vasopressin Receptor Expression in Cultured Cells, The Journal of Biological chemistry, pp. 14599-14605, No. 24, 1990.
Salo, J., et al., Effect of Therapeutic Paracentesis on Plasma Volume and Transvascular Escape Rate of Albumin in Patients with Cirrhosis, Journal of Hepatology, pp. 645-653, 1997.
Møller, S., et al., Central and Systemic Haemodynamic Effects of Terlipressin in Portal Hypertensive Patients, pp. 51-59, Liver, 2000.

* cited by examiner

*Primary Examiner*—B. Dell Chism
(74) *Attorney, Agent, or Firm*—Townsend and Townsend and Crew LLP

(57) ABSTRACT

The present invention relates to an improved method for the treatment of hypovolaemia or hypotension associated with therapeutic paracentesis, which method is characterised by the use of a peptide according to general formulae (I) or a salt thereof, wherin Asn, Cys, Gln, Gly, Phe and Pro represent the amino acid residues asparigine, cysteine, glutamine, glycine, phenylalanine and proline respectively; Phe(X) represents a phenylalanine residue optionally substituted at the 4-position of the aromatic ring by a group selected from methyl, ethyl, hydroxy and methoxy; Y represents a group —$(CH_2)_a$—NH-Q, where a is 2–5 and Q is H or C(=NH)$NH_2$; and R represents a chain of between two and for αalpha-amino acid residues, at least one of which is glycine, as the active agent. The invention also provides uses of the peptide and pharmaceutical compositions.

13 Claims, No Drawings

PROTOCOL FOR PARACENTESIS

The present invention relates to an improved method for the management of ascites in cirrhotic individuals, and specifically for the control of hypotension following paracentesis.

BACKGROUND

Cirrhosis of the liver is a common consequence of excessive alcohol consumption or hepatitis. In about 30% of cases of cirrhosis there is a build up of fluid in the peritoneal cavity. This is usually controlled by paracentesis. This procedure is frequently complicated by hypovolaemia and a fall in arterial blood pressure. The usual method for controlling this undesirable side effect is to administer an infusion of human albumin. However, because human albumin is derived from donated human blood, there is a risk that pathogens may be transmitted during the treatment. There is also a financial consideration. Even though it is sourced from voluntary donations in many countries, human albumin is expensive, and paracentesis is generally repeated on a biweekly basis for up to two years (depending on the availability of a suitable liver for transplantation).

Overall then, there exists a need for a better method for the control of hypotension following paracentesis. To reduce the risk of infection the method should not involve the use of a product of human origin, and preferably the cost of the treatment should be reduced.

BRIEF DESCRIPTION OF THE INVENTION

We have now found that terlipressin, a synthetic peptide previously used in the control of bleeding oesophagal varices, can be used in place of human albumin for the control of hypotension following paracentesis. Because terlipressin is a product of chemical synthesis it is not associated with any risk of contamination by human pathogens. The use of terlipressin in place of human albumin gives an equivalent clinical outcome, and the cost of the treatment is reduced. Furthermore, because terlipressin can be administered as a bolus injection rather than the infusion required for albumin, the protocol is more convenient for the patent.

The present invention therefore comprises, in a first aspect, an improved method for the control of hypotension following paracentesis, particularly in cases of cirrhosis of the liver.

In a second aspect, the present invention comprises a new use for terlipressin, which use is as an agent for the control of hypotension following paracentesis. In a third aspect, the invention comprises a pharmaceutical composition for the control of hypotension following paracentesis, which composition is a solution of terlipressin for infusion.

Certain analogues of terlipressin may be considered as being equivalent to terlipressin for the purposes of the present invention.

DETAILED DESCRIPTION OF THE INVENTION

In a first aspect, the present invention comprises an improved method for the control of hypovolaemic hypotension associated with paracentesis. The method is characterised in that the therapeutic agent used to control the hypotension is terlipressin, or an analogue thereof. Suitable analogues are disclosed in U.S. Pat. No. 3,558,590 and its equivalents (such as French Patent No. 1,492,017, UK Patent No. 1,106,536, German Patent No. 1 493 561). They are described by general formula 1:

wherein Cys, Phe, Gin, Asn, Pro and Gly represent the amino add residues cysteine, phenylatamine, glutamine, asparigine, proline and glycine respectively, Phe(X) represents a phenylalanine residue optionally substituted at the 4-position of the aromatic ring by a group selected from methyl, ethyl, hydroxy and methoxy, Y represents a chain of between two and five methylene groups with a basic group such as amino or guanidino on the terminal methylene group, and R represents a chain of between two and four α-amino acid residues, at least one of which is glycine.

Preferably, the peptide is Terlipressin, which is a compound according to general formula 1 in which R represents Gly-Gly-Gly; Phe(X) represents tyrosine; and Y represents $(CH_2)_4NH_2$.

Terlipressin, also known as GLYPRESSIN® or triglycyl lysine vasopressin, is a synthetic peptide. It is an analogue of vasopressin, which is an endogenous vasoactive hormone. Terlipressin is currently approved as a haemostatic agent for the treatment of bleeding oesophagal varices.

Due to its chemical nature, terlipressin is capable of forming salts with acids such as acetic acid and hydrochloric acid. All references to terlipressin in this document should be considered to include both the free base and all such salts, and apply particularly to the acetate salt that is the form actually marketed.

In a preferred embodiment, the paracentesis is required to relieve ascites due to cirrhosis of the liver. While no causative factors are excluded, the method is particularly applicable to cases of cirrhosis due to excessive alcohol consumption or to hepatitis (including hepatitis B and hepatitis C).

In another preferred embodiment, the terlipressin is administered by intravenous injection. A course of treatment may involve a single injection, or repeated injections. Preferably, the course of treatment comprises an injection immediately before the start of the paracentesis and one or more (such as two or three) injections following the paracentesis. A particularly preferred course of treatment comprises one injection prior to paracentesis and two injections afterwards. The injections may be separated by a period of a few hours, such as a period of between 4 and 12 hours, more preferably between 6 and 10 hours. A most preferred course of treatment comprises an injection before the, start of the paracentesis and follow-up injections 8 and 16 hours later.

The amount of terlipressin to be administered will be determined by the responsible physician, taking into consideration all the relevant factors. In a preferred embodiment of the invention, the amount of terlipressin administered in each injection is between 0.1 mg and 10 mg. More preferably it is between 0.2 mg and 5 mg, and most preferably between 0.5 mg and 2 mg.

In a second aspect, the present invention comprises a new medical use for the known therapeutic agent that is terlipressin. This new use is as an agent for the treatment of hypovolaemic hypotension due to paracentesis, particularly where the paracentesis is necessary to treat ascites in a person suffering from cirrhosis of the liver.

In a preferred embodiment, the cirrhosis is a consequence of excessive alcohol consumption or hepatitis.

In another preferred embodiment, the terlipressin is administered by intravenous injection. More preferably, it is administered in more than one intravenous injection. Most preferably, it is administered by an intravenous injection before the start of the paracentesis and two further injections after the paracentesis.

In a further preferred embodiment, the injections of terlipressin are separated by a period of a few hours, such as a period of between 4 and 12 hours, more preferably between 6 and 10 hours, most preferably a period of 8 hours.

In another preferred embodiment, the amount of terlipressin administered is between 0.1 mg and 10 mg per injection, more preferably between 0.2 mg and 5 mg, most preferably between 0.5 mg and 2 mg.

In a third aspect, the present invention comprises a pharmaceutical composition for the treatment of hypovolaemic hypotension due to paracentesis, particularly paracentesis to treat ascites due to cirrhosis of the liver. The composition is characterised in that the active pharmaceutical agent is terlipressin. The composition may further comprise such pharmaceutically acceptable agents as are known in the art. Such agents may include preservatives, bulking agents, solvents and the like.

In a preferred embodiment, the composition is intended for intravenous injection and so comprises a solvent. A preferred solvent is water, such as pyrogen-free water for injection according the European Pharmacopeia. Another preferred solvent is isotonic saline. The composition may be presented as a pre-prepared solution ready for use. Alternatively it may be presented as a kit comprising a vial or other suitable vessel containing a measured quantity of terlipressin and another vial containing the solvent, such that the solution of terlipressin can be prepared immediately prior to use.

The foregoing description of the present invention is further illustrated in the following Example. The Example describes a clinical study in which terlipressin and human albumin were compared directly. The protocol described should not be considered to be limiting as to the scope of the present invention.

EXAMPLE

Comparison of the Effect of Terlipressin and Albumin in Patients Treated by Paracentesis Patient selection criteria: 24 clinically stable cirrhotic patients with tense ascites in need of therapeutic paracentesis were recruited to the study. Four were subsequently excluded prior to treatment. Patients were randomly allocated to either the terlipressin or the albumin treatment group. Useful data was obtained for 10 patients in each group. Table 1 summarises the clinically relevant characteristics of the two groups.

TABLE 1

Characteristics of two treatment groups

|  | Terlipressin group (n = 10) | Albumin group (n = 10) |
| --- | --- | --- |
| Age (years) | 50 ± 2 | 58 ± 2 |
| Sex (M/F) | 8/2 | 8/2 |
| Alcoholic cirrhosis | 8 | 8 |
| Beta blockers | 3 | 3 |
| Bilirubinaemia (μmol/L) | 44 ± 13 | 39 ± 5 |
| Albuminaemia (g/L) | 28.4 ± 2.0 | 29.6 ± 2.0 |
| PT (%) | 58 ± 5 | 49 ± 3 |
| Pugh score | 9.4 ± 0.5 | 9.6 ± 0.2 |
| Pugh grade |  |  |
| B | 6 | 6 |
| C | 4 | 4 |

Treatment: Both groups received therapeutic paracentesis according to the usual protocol of the study centre. One group received 20% human albumin at a dose of 8 g per liter of removed ascitic fluid. The other group received 1 mg of terlipressin GLYPRESSIN® (triglycyl lysine vasopressin), Laboratoire F ring. Gentilly, France) as an intravenous bolus injection prior to paracentesis, and further 1 mg injections 8 and 16 hours later (total dose 3 mg). Plasma renin and aldosterone levels were measured as markers of blood volume. Certain other parameters were determined as secondary criteria for successful treatment. The results are summarised in Table 2.

TABLE 2

Results of treatment

|  | Terlipressin group (n = 10) | | Albumin group (n = 10) | |
| --- | --- | --- | --- | --- |
| Removed ascitic fluid volume (L) | 6 ± 1 | | 5 ± 1 | |
| Period between paracentesis treatment and discharge from hospital (days) | 5.5 ± 0.2 | | 5.3 ± 0.3 | |
| Survival at 3 months (%) | 86 | | 89 | |
|  | Before | 4–6 days later | Before | 4–6 days later |
| Reninaemia (pg/mL) | 156 ± 81 | 130 ± 34 | 194 ± 47 | 223 ± 74 |
| Aldosteronaemia (pg/mL) | 1017 ± 278 | 1337 ± 280 | 1149 ± 324 | 1420 ± 292 |
| Weight (kg) | 77 ± 4 | 73 ± 3 | 72 ± 5 | 69 ± 4 |
| Blood pressure (mmHg) | 79 ± 3 | 78 ± 3 | 81 ± 4 | 79 ± 3 |
| Creatininaemia | 75 ± 9 | 72 ± 8 | 74 ± 4 | 71 ± 6 |
| Natraemia (mmol/L) | 134 ± 1 | 133 ± 1 | 134 ± 1 | 132 ± 1 |

It is apparent from the above results that terlipressin and albumin are equally effective in treating hypovolaemia (as indicated by the values for reninaemia and aldosteronaemia). Other parameters, including time to discharge from hospital and medium term survival are also comparable. The conclusion drawn is that terlipressin treatment is a valid alternative to the use of human albumin in the control of hypovolaemic hypotension following paracentesis. Furthermore, the use of terlipressin eliminates the risk of infection associated with the use of a therapeutic agent derived from human blood, and the cost of treatment is reduced. In the study described in the Example above, the cost per treatment with terlipressin was €990, compared to a cost per treatment with albumin of €1100. Finally, since terlipressin can be administered as a bolus injection while albumin is administered by infusion, the protocol is more convenient for the patient and the medical staff involved.

The invention claimed is:

1. A method for the treatment of hypovolaemia or hypotension in a subject in need thereof following or during therapeutic paracentesis, comprising administering a peptide according to the general formulae 1 or a salt thereof to said subject following or during therapeutic paracentesis,

1 wherein:
   Asn, Cys, Gln, Gly, Phe and Pro represent the amino acid residues asparigine, cysteine, glutamine, glycine, phenylalanine and proline respectively;
   Phe (X) represents a phenylalanine residue optionally substituted at the 4-position of the aromatic ring by a group selected from methyl, ethyl, hydroxy and methoxy;
   Y represents a group —$(CH2)_a$—NH-Q, where a ranges from 2–5 inclusive and Q is H or C(=NH)NH$_2$; and
   R represents a chain of between two and four α-amino acid residues, at least one of which is glycine, as the active agent.

2. A method according to claim 1, wherein the peptide is terlipressin, or a salt thereof, as the active agent.

3. A method according to claim 1, wherein the therapeutic paracentesis is necessary to relieve ascites resulting from cirrhosis of the liver.

4. A method according to claim 3, wherein the cirrhosis of the liver is a result of excessive alcohol consumption or hepatitis.

5. A method according to claim 2 wherein the terlipressin is administered by intravenous injection.

6. A method according to claim 5 wherein the terlipressin as administered as a single injection prior to the start of the paracentesis and one or more injections after the paracentesis.

7. A method according to claim 6 wherein the terlipressin is administered as a single injection prior to the start of the paracentesis and two injections after the paracentesis.

8. A method according to claim 6 wherein the injections are separated by an interval of between 4 and 12 hours.

9. A method according to claim 6 wherein the injections are separated by an interval of between 6 and 10 hours.

10. A method according to claim 6 wherein the injections are separated by an interval of approximately 8 hours.

11. A method according to claim 2 wherein the amount of terlipressin given at each administration is between 0.1 mg and 10 mg.

12. A method according to claim 2 wherein the amount of terlipressin given at each administration is between 0.2 mg and 5 mg.

13. A method according to claim 2 wherein the amount of terlipressin given at each administration if between 0.5 mg and 2 mg.

* * * * *